United States Patent
Lin et al.

(10) Patent No.: US 7,232,669 B1
(45) Date of Patent: Jun. 19, 2007

(54) PROCESS FOR ENHANCING ANAEROBIC BIOHYDROGEN PRODUCTION

(75) Inventors: Ping-Jei Lin, Taichung (TW); Kuo-Shing Lee, Taichung (TW); Jo-Shu Chang, Taichung (TW); Yi-Sheng Chang, Taichung (TW); Yu-Shin Huang, Taichung (TW)

(73) Assignee: Feng Chia University, Taichung (TW)

( * ) Notice: Subject to any disclaimer, the term of this patent is extended or adjusted under 35 U.S.C. 154(b) by 0 days.

(21) Appl. No.: 11/586,957

(22) Filed: Oct. 26, 2006

(30) Foreign Application Priority Data

Mar. 10, 2006 (TW) ............................... 95108117 A

(51) Int. Cl.
*C12P 3/00* (2006.01)
(52) U.S. Cl. ..................................... 435/168
(58) Field of Classification Search ................. 435/168
See application file for complete search history.

(56) References Cited

U.S. PATENT DOCUMENTS

| 5,821,111 | A | * | 10/1998 | Grady et al. ............. 435/252.5 |
| 5,942,424 | A | * | 8/1999 | Woodward et al. ......... 435/168 |
| 6,942,998 | B1 | * | 9/2005 | Ooteghem ................... 435/168 |
| 2005/0064567 | A1 | * | 3/2005 | Lay et al. .................... 435/168 |

FOREIGN PATENT DOCUMENTS

TW          I186706          1/2004

OTHER PUBLICATIONS

Levin, et al., "Biohydrogen production: prospects and limitations to practical application", International Journal of Hydrogen energy, vol. 29, pp. 173-185 (2004).
Das, et al., "Hydorgen production by biological processes: a survey of literature", International Journal of Hydrogen energy, vol. 26, pp. 13-28 (2004).
Lin, et al., "Hydrogen production during the anaerobic acidogenic conversion of glucose", Journal of Chemical Technology and Biotechnology, vol. 74, pp. 498-500 (1999).
Mizuno, et al., "Enhancement of hydrogen production from glucose by nitrogen gas sparging"., Bioresource Technology, vol. 73, pp. 59-65(2000).
Chen, et al., "Kinetics of hydrogen production with continuous anaerobic cultures utilizing sucrose as the limiting substrate", Appl Microbiol Biotechnol, vol. 57, pp. 56-64 (2001).
Fang, et al., "Characterization of a Hydrogen-Producing Granular Sludge", Biotechnology and Bioengineering, vol. 78, No. 1, pp. 44-52 (2002).
Horiuchi, et al., "Selective production of organic acids in anaerobic acid reactor by pH control", Bioresource Technology, vol. 82, pp. 209-213 (2002).
Liu, et al., "Hydrogen production from wastewater by acidogenic granular sludge", Water Science and Technology, vol. 47, No. 1, pp. 153-158 (2002).
Taiwan Publication No. TW553898B, Published Sep. 21, 2003, Lin, et al., "Method for promoting generation of hydrogen from biological sludge by heat pretreatment".
Taiwan Publication No. TW200417533, Published Sep. 16, 2004, Lai, et al., "Microbial Production of Hydrogen Under Anaerobic Condition" (Abstract only).

* cited by examiner

*Primary Examiner*—Herbert J. Lilling
(74) *Attorney, Agent, or Firm*—Law Offices of Albert Wai-Kit Chan, PLLC

(57) ABSTRACT

Disclosed herein is a process for enhancing anaerobic biohydrogen production, including: adding into a reactor an organic waste containing hydrogen-producing anaerobic bacteria, a first substrate, and a carrier that permits the hydrogen-producing anaerobic bacteria to adhere and grow thereon, so as to form a mixture; acclimating the mixture at a first agitation speed ranging from 5 to 60 rpm, so that the hydrogen-producing anaerobic bacteria adhere to and proliferate on the carrier, followed by the formation of granular biomasses within the acclimated mixture; and feeding a second substrate into the reactor at a second agitation speed ranging from 5 to 60 rpm, so that the content of the granular biomasses is increased while the second substrate is anaerobically fermented by the hydrogen-producing anaerobic bacteria in the granular biomasses to result in the production of hydrogen.

23 Claims, 5 Drawing Sheets

PROCESS FOR ENHANCING ANAEROBIC BIOHYDROGEN PRODUCTION

CROSS-REFERENCE TO RELATED APPLICATION

This application claims priority of Taiwanese Patent Application No. 095108117, filed on Mar. 10, 2006.

BACKGROUND OF THE INVENTION

1. Field of the Invention

This invention relates to a process for enhancing anaerobic biohydrogen production, which includes adding into a reactor an organic waste containing hydrogen-producing anaerobic bacteria, a first substrate, and a carrier that permits the hydrogen-producing anaerobic bacteria to adhere thereto and to grow thereon, so as to form a mixture; acclimating the mixture at a first agitation speed ranging from 5 to 60 rpm, so that the hydrogen-producing anaerobic bacteria adhere to and proliferate on the carrier, followed by the formation of granular biomasses constituted of the hydrogen-producing anaerobic bacteria within the acclimated mixture; and feeding a second substrate into the reactor at a second agitation speed ranging from 5 to 60 rpm, so that the content of the granular biomasses is increased while the second substrate is anaerobically fermented by the hydrogen-producing anaerobic bacteria in the granular biomasses to result in the production of hydrogen.

2. Description of the Related Art

Recently, hydrogen has attracted wide attention and is regarded as one of the important energy sources of the future because it has the advantages of cleanness, non-polluting, good recyclability, and high heat energy (D. B. Levin et al. (2004), *International Journal of Hydrogen Energy*, 29:173-185).

Hydrogen production methods can be classified into three main types, namely, the thermochemical method, the electrochemical method, and the biological method.

The thermochemical method includes steam reforming of methane, coal gasification, partial oxidation of hydrocarbon compounds, etc. These hydrogen production methods have been industrialized, but since consumption of a large amount of mineral resources and energy is required and pollutants harmful to the environment are generated during the production process, they do not contribute to the development of energy resources.

Although the electrochemical method (e.g., electrolysis, photoelectrolysis, etc.) does not engender environment pollution, and the purity of hydrogen produced thereby is relatively high, it still has problems of low efficiency, high energy consumption, unsatisfactory electrode stability, etc., which remain to be solved (D. Das et al. (2001), *International Journal of Hydrogen Energy*, 26:13-28).

In contrast, the cost required to produce hydrogen using biodegradation is relatively low, and is therefore more advantageous than chemical hydrogen production methods. The biological hydrogen production method includes: (1) biophotolysis of water, which is the use of photo-induction to encourage algae or cyanobacteria to decompose water so as to result in the production of hydrogen; (2) photo-fermentation, which is the use of photosynthetic bacteria to decompose organic matters so as to result in the production of hydrogen; and (3) dark-fermentation, which is the use of anaerobic bacteria to decompose organic matters to result in the production of hydrogen. Biophotolysis of water and photo-fermentation require a higher reaction free energy, whereas dark-fermentation does not require a light source and can utilize various organic matters as substrates. Therefore, in industrial applications, dark-fermentation hydrogen production techniques have been extensively used to process organic waste.

Use of anaerobic bacteria to process organic matter-containing wastewater or waste (e.g., kitchen leftovers, wastes of agricultural or energy crops, and wastewater or waste of organic industries, etc.) not only can produce hydrogen for use as energy, organic acids can also be produced for re-use. Besides, expenses associated with processing of various kinds of sludge and organic wastewater or waste can be reduced.

The design of a conventional anaerobic fermentative reaction system primarily attempts to shorten the hydraulic retention time (HRT) of system operation so as to increase the organic loading rate (OLR) of the system, while trying to enhance the degradation rate by increasing the concentration of hydrogenogenic bacteria or the activity of sludge, thereby achieving the objective of enhancing the efficiency of biological wastewater treatment (G. Lettinga et al., (1980), *Biotechnology and Bioengineeting*, 22:699-734).

Conventional continuous stirred tank reactors (CSTR) have extensive applications in the study of anaerobic fermentative hydrogen production because of simple system operation and good mixing capability. Regarding studies in this respect, reference can be made to, for instance, C. Y. Lin et al., (1999), *Journal of Chemical Technology and Biotechnology*, 74:498-500; 0. Mizuno et al., (2000), *Bioresource Technology*, 73:59-65; C. C. Chen et al., (2001), *Appl Microbiol Biotechnol.*, 57:56-64; H. H. P. Fang et al., (2002), *Biotechnology and Bioengineering*, 78:44-52; J. I. Horiuchi et al., (2002), *Bioresource Technology*, 82:209-213; H. Liu et al., (2002), *Water Science and Technology*, 47(1): 153-158; and J. S. Chang et al., "Using Environmental Biological Techniques to Produce a Clean Energy—Hydrogen," Chemical Engineering, Volume 49, No. 6, 85-104, December, 2002.

However, these prior studies show that when the continuous stirred tank reactor is used to conduct an anaerobic fermentative hydrogen production reaction under a relatively low hydraulic retention time, wash-out often occurs between the fed substances and microorganisms so that concentration of biomasses containing hydrogenogenic bacteria drops, thereby reducing the hydrogen production efficiency. For example, Chang et al. discovered that, when the continuous stirred tank reactor operates under the condition that HRT$\geq$4 hr., wash-out of the hydrogenogenic bacteria-containing biomasses in the tank reactor will occur, which is detrimental to the process of anaerobic fermentative hydrogen producing reaction [Chang et al. (2002), supra].

In TW 200417533 of Lai et al., there is disclosed a process for anaerobic hydrogen production, which includes the following steps: (1) crushing waste into granular particles with a length and width less than 1 mm and mixing the same with water; (II) pre-treatment and formulation of seeding material; (III) anaerobic fermentation to produce hydrogen; (IV) anaerobic fermentation to produce methane gas; and (V) purification of discharged gas from the hydrogen production fermentation tank. In step (III), if a batch reaction is conducted, the rotational speed of the reactor is between 25 and 35 rpm. On the other hand, if a continuous reaction is conducted, the rotational speed of the reactor is between 30 and 100 rpm.

In addition, Lee et al. disclose a biohydrogen production technique, in which spherical activated carbon and cylindrical activated carbon are used as carriers, and are filled into a fixed bed reactor for hydrogenogenic bacteria to adhere thereto and to grow thereon so as to form a biofilm. The aforesaid technique can effectively maintain the concentration of hydrogenogenic bacteria in the reactor and suppress occurrence of wash-out so that anaerobic fermentative hydrogen reaction can be stably conducted under operating conditions of a low hydraulic retention time and a high organic loading rate (Lee et al., Continuous Hydrogen Fermentation Using a Biofilm Reactor, *Proceedings of the 7th Biochemical Engineering Symposium*, Jun. 28-29, 2002).

According to this prior study, when a fixed bed reactor having a 0.3 L or 3 L working volume is used to conduct an anaerobic fermentative hydrogen production reaction, hydrogen can be produced stably at a hydraulic retention time of 1 hour. The hydrogen production rate (HPR) is approximately 1.21 L/h/L, whereas the hydrogen content ($H_2$ content) can reach approximately more than 30%. However, when the hydraulic retention time is lowered to 0.5 hour, the anaerobic fermentative reaction system will show signs of instability, thereby resulting in a lowered hydrogen production rate.

Therefore, there still exists a need to develop a new anaerobic biohydrogen production technique, which can achieve an excellent hydrogen production efficiency even under operating conditions of a low hydraulic retention time and a high organic loading rate.

SUMMARY OF THE INVENTION

Accordingly, the present invention provides a process for enhancing anaerobic biohydrogen production, which includes:

adding into a reactor an organic waste containing hydrogen-producing anaerobic bacteria, a first substrate, and a carrier that permits the hydrogen-producing anaerobic bacteria to adhere and grow thereon, so as to form a mixture;

acclimating the mixture at a first agitation speed ranging from 5 to 60 rpm, so that the hydrogen-producing anaerobic bacteria adhere to and proliferate on the carrier, followed by the formation of granular biomasses constituted of the hydrogen-producing anaerobic bacteria within the acclimated mixture; and feeding a second substrate into the reactor at a second agitation speed ranging from 5 to 60 rpm, so that the content of the granular biomasses is increased while the second substrate is anaerobically fermented by the hydrogen-producing anaerobic bacteria in the granular biomasses to result in the production of hydrogen.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE INVENTION

Figure 1:
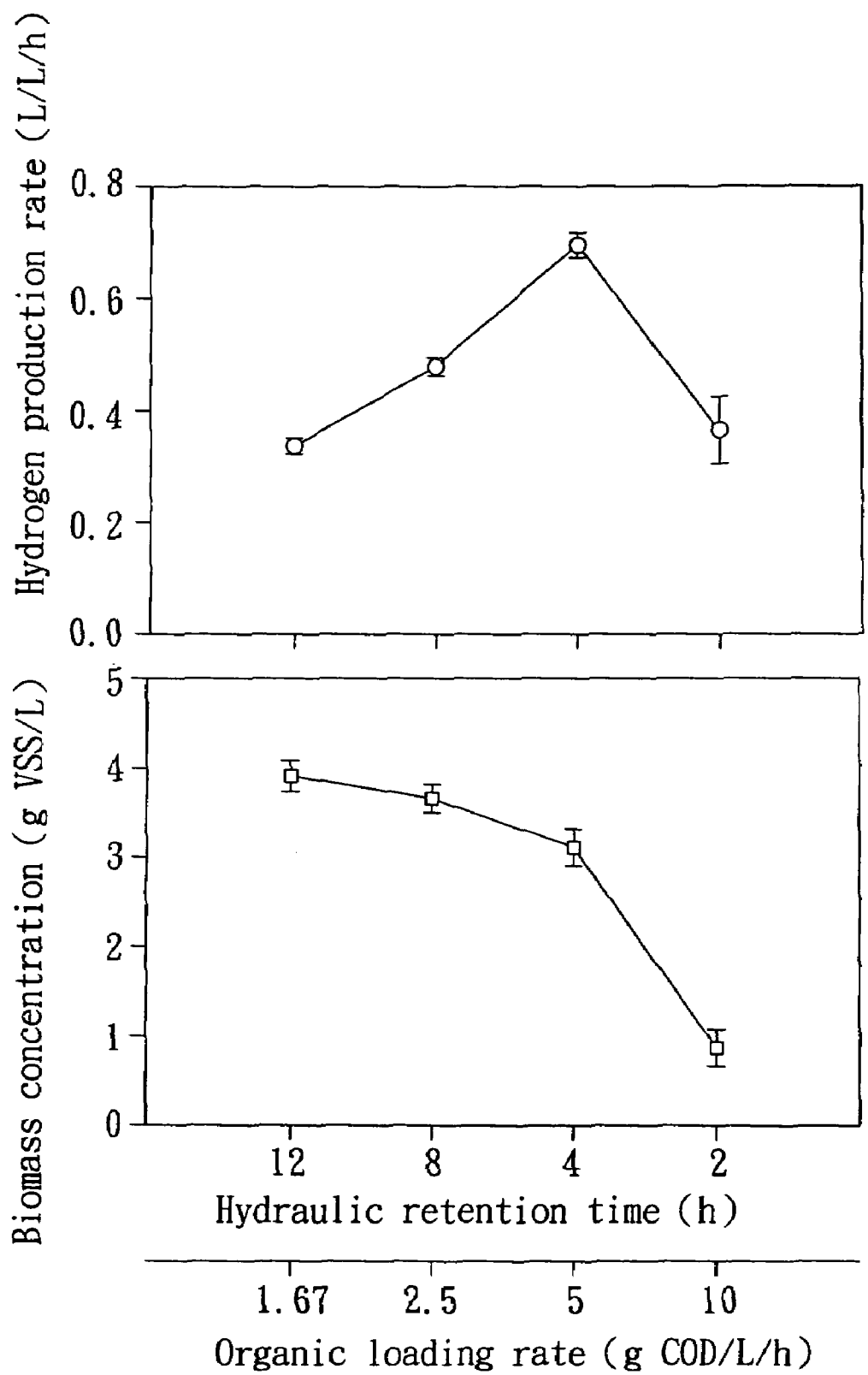
FIG. 1 shows the hydrogen production rates and the biomass concentrations (expressed in mean±standard error, number of samples being about 3 to 8) respectively detected when anaerobic fermentative reactions were carried out at an agitation speed of 150 rpm and at different hydraulic retention times, using sucrose (at a concentration of 20 g chemical oxygen demand (COD)/L) as a substrate.

After doing extensive researches, the applicant, in this invention, provides a process for enhancing anaerobic biohydrogen production, which includes:

adding into a reactor an organic waste containing hydrogen-producing anaerobic bacteria, a first substrate, and a carrier that permits the hydrogen-producing anaerobic bacteria to adhere thereto and to grow thereon so as to form a mixture;

acclimating the mixture at a first agitation speed ranging from 5 to 60 rpm, so that the hydrogen-producing anaerobic bacteria adhere to and proliferate on the carrier, followed by the formation of granular biomasses constituted of the hydrogen-producing anaerobic bacteria within the acclimated mixture; and feeding a second substrate into the reactor at a second agitation speed ranging from 5 to 60 rpm, so that the content of the granular biomasses is increased while the second substrate is anaerobically fermented by the hydrogen-producing anaerobic bacteria in the granular biomasses to result in the production of hydrogen.

According to the present invention, the organic waste may be, but is not limited to, sewage sludge from household wastewater treatment plants; sewage sludge from fermentation-related industries, such as monosodium glutamate manufacturing industries, wine or alcohol manufacturing industries, and vinegar manufacturing industries; sewage sludge from paper manufacturing industries; sewage sludge from sugar manufacturing industries; sewage sludge from food factories; and combinations thereof. In a preferred embodiment of the invention, the organic waste is sewage sludge from a household wastewater treatment plant.

According to the present invention, the organic waste may be subjected to a pretreatment. The pretreatment may help suppress growth and/or bioactivity of methanogenic bacteria and/or undesirable microorganisms (e.g., hydrogen-consuming bacteria) that may be present in the organic waste, so that the hydrogen-producing anaerobic bacteria contained in the organic waste are dominant.

Pretreaments suitable for the organic waste may be, but are not limited to, heating, acclimation, treatment using a pH adjusting agent, and combinations thereof.

According to the present invention, the organic waste is subjected to heat pretreatment at a temperature ranging from 80 to 120° C. for a sufficient period of time, e.g., 20 to 60 minutes. In a preferred embodiment of the present invention, the organic waste is subjected to heat pretreatment at a temperature ranging from 90 to 100° C. for 30 to 60 minutes.

According to the present invention, techniques known and commonly used by those skilled in the art can be adopted to acclimate the organic waste. In this respect, reference can be made to, e.g., C. C. Chen et al., (2001), *Appl. Microbiol. Biotechnol.*, 57:56-64.

According to the present invention, the organic waste may be pretreated using an acidic pH adjusting agent so as to have a pH value ranging from 3 to 5. In addition, the choice of the acidic pH adjusting agent should not affect the bioactivity of the organic waste. Preferably, the acidic pH adjusting agent is selected from the group consisting of hydrochloric acid, sulfuric acid, nitric acid, and combinations thereof.

According to the present invention, the organic waste may be pretreated using a basic pH adjusting agent so as to have a pH value ranging from 10 to 12. In addition, the choice of the basic pH adjusting agent should not affect the bioactivity of the organic waste. Preferably, the basic pH adjusting agent is a metal hydroxide, such as NaOH, KOH, LiOH, $Ca(OH)_2$, $Mg(OH)_2$, etc.

According to the present invention, the first substrate and the second substrate are independently selected from the group consisting of an artificial substrate and an organic waste.

Artificial substrates suitable for the present invention include a saccharide selected from the group consisting of glucose, fructose, xylose, sucrose, maltose, starch, and combinations thereof. In a preferred embodiment of the present invention, the artificial substrate includes glucose. In another preferred embodiment of the present invention, the artificial substrate includes sucrose.

Organic wastes suitable for use as the first substrate or the second substrate according to the present invention may be, but are not limited to, sewage sludge from household wastewater treatment plants, sewage sludge from fermentation-related industries, such as monosodium glutamate manufacturing industries, wine or alcohol manufacturing industries, and vinegar manufacturing industries, sewage sludge from sugar manufacturing industries, sewage sludge from food factories, etc. Preferably, the organic waste suitable for use as the first substrate is molasses-containing sewage sludge from fermentation-related industries or food factories.

According to the present invention, the carrier is a microporous adsorbent, including, but not limited to, powdered activated carbon, powdered diatomaceous earth, zeolite, and combinations thereof. In a preferred embodiment of the present invention, the microporous adsorbent is powdered activated carbon with a particle size less than 44 microns (more than 325 mesh), and has a large specific surface area so that hydrogen-producing anaerobic bacteria in the organic waste can adhere thereto and proliferate thereon.

Reactors suitable for the present invention are reactors equipped with a stirrer device in a fermentation tank, including, but not limited to, a continuous stirred tank reactor (CSTR), an anaerobic sequencing batch reactor (ASBR), an anaerobic baffled bioreactor (ABR), a carrier-induced granular sludge bed (CIGSB), an upflow anaerobic sludge blanket (UASB), an expanded granular sludge bed (EGSB), etc. In a preferred embodiment of the present invention, the reactor is a continuous stirred tank reactor (CSTR). In another preferred embodiment of the present invention, the reactor is an upflow anaerobic sludge blanket (UASB).

It should be appreciated that the operating conditions of the reactor can be varied with factors like the peripheral instruments and equipment used, the type of reactant (e.g., the organic waste, the first substrate, and the second substrate), the proportion of the amounts used, the type of pretreatment, etc, so as to achieve an optimum hydrogen production effect. The choice of these operating conditions can be routinely determined by those skilled in the art on their own.

According to the present invention, the organic waste, the first substrate and the carrier can be mixed in a reactor placed in an anaerobic state so as to form a mixture.

According to the present invention, the anaerobic state of the reactor can be achieved by evacuation. As an alternative, the anaerobic state of the reactor can be achieved by filling the reactor with an inert gas. Inert gases suitable for the present invention may be selected from the group consisting of helium, argon, neon, krypton, xenon, and combinations thereof. Preferably, the inert gas is argon.

Preferably, the first agitation speed and the second agitation speed are independently set to fall within a range from 5 to 45 rpm. More preferably, the first agitation speed and the second agitation speed are independently set to fall within a range from 5 to 30 rpm. Most preferably, the first agitation speed and the second agitation speed are independently set to fall within a range from 15 to 20 rpm. In a preferred embodiment of the present invention, the mixture formed from the organic waste, the first substrate and the carrier is acclimated at a first agitation speed of 15 to 20 rpm, whereas the second substrate is fed into the reactor at a second agitation speed of 15 to 20 rpm. When the present invention is adapted for use in large scale production, the first agitation speed and the second agitation speed can be up-adjusted to a range not exceeding 60 rpm in accordance with the volume of the reactor.

According to the present invention, the second substrate can be fed into the reactor at a hydraulic retention time ranging from 0.5 to 8 hours. Preferably, the second substrate is fed into the reactor at a hydraulic retention time ranging from 0.5 to 4 hours.

According to the present invention, the second substrate can be fed into the reactor at an organic loading rate ranging from 5 to 80 g COD/L/h. Preferably, the second substrate is fed into the reactor at an organic loading rate ranging from 20 to 80 g COD/L/h.

According to the present invention, the second substrate may be fed continuously or intermittently into the reactor depending on requirements. In a preferred embodiment of the present invention, the second substrate is fed continuously into the reactor.

Accordingly, the present invention provides a convenient, energy-saving process for biohydrogen production to enable manufacturers to effectively utilize organic wastes as a hydrogen-producing energy source. Particularly, according to the process of the present invention, a carrier is used to permit hydrogen-producing anaerobic bacteria in the organic waste to adhere thereto and to proliferate thereon. At the same time, anaerobic fermentative hydrogen production reactions conducted at a low agitation speed (e.g., approximately 15 to 20 rpm) can enhance the formation of granular biomasses of the anaerobic fermentative reaction system used, so that the anaerobic fermentative reaction system can produce hydrogen stably and very efficiently under the operating conditions of a low hydraulic retention time (e.g., approximately 0.5 to 4 hr.) and a high organic loading rate (e.g., approximately 20 to 80 g COD/L/h).

The present invention will be further described by way of the following examples. However, it should be understood that the following examples are intended for the purpose of illustration only and should not be construed as limiting the present invention in practice.

EMBODIMENTS

A. Experimental Materials:
1. In the following examples, the organic waste for use as the seeding sludge was obtained from the sewage sludge from Li-ming Municipal Sewage Treatment Plant in Taichung City. The properties thereof are shown in Table 1.

TABLE 1

Properties of sewage sludge

| Items tested | Numerical Value |
| --- | --- |
| pH | 6.8 |
| Volatile suspended solid (VSS)(g/L) | 33.3 |
| Total suspended solid (TSS)(g/L) | 65.1 |

2. In the following examples, the formulation of nutrient salts makes reference to the method described by G. Endo et al., (1982) in *Proc. Soc. Civ. Engrs,* 325:61-68. The ingredients thereof are shown in the following Table 2.

TABLE 2

Formulation of Nutrient Salts

| Ingredients | Concentration (mg/L) |
| --- | --- |
| $NH_4Cl$ | 717 |
| $NaHCO_3$ | 15000 |
| $K_2HPO_4$ | 125 |
| $CaCl_2$ | 100 |
| $MgCl_2 \cdot 6H_2O$ | 100 |
| $MnSO_4 \cdot 6H_2O$ | 15 |
| $FeSO_4 \cdot 7H_2O$ | 25 |
| $CuSO_4 \cdot 5H_2O$ | 2 |
| $CoCl_2 \cdot 5H_2O$ | 0.125 |

3. In the following examples, glucose or sucrose was used in the acclimation of the seeding sludge and as the artificial substrate in anaerobic fermentative hydrogen production.
4. In the following examples, the carrier for the hydrogen-producing anaerobic bacteria to adhere thereto and to grow thereon is powdered activated carbon, which was purchased from Taiwan Carbon Industrial Co., Ltd. The properties thereof are shown in the following Table 3.

TABLE 3

Physical Properties of Powdered Activated Carbon

| Properties | Numerical Values |
| --- | --- |
| Particle size (μm) | <44 |
| Bulk density (g/ml) | 0.25-0.35 |
| Specific surface area($m^2/g$) | >1200 |

B. General Operating Methods and Equipment:
1. Continuous stirred tank reactor (CSTR): It has a working volume of 1 L.
2. Upflow Anaerobic Sludge Blanket (UASB): It has a working volume of 1.25 L, and has a stirrer additionally mounted therein.
3. Heat pretreatment of seeding sludge:
   In the following experiments, the heat pretreatment of the seeding sludge was performed with reference to the method disclosed by Chiou-Yu Lin et al. in TW 553898. Principally, the sewage sludge from Li-ming Municipal Sewage Treatment Plant, Taichung City, was subjected to heat pretreatment at a temperature ranging from 80° C. to 120° C. for 30 to 60 minutes such that the bioactivity of the methanogenoic bacteria in the sewage sludge was suppressed, and *Clostridium* sp. became dominant.
4. Analysis of gas composition:
   In the following experiments, a gas chromatograph (SHIMADZU GC-14B) equipped with a thermal conductivity detector (TCD) was used to conduct an analysis of gas composition.
5. Analysis of biomass concentration:
   In the following experiments, the analysis of biomass concentration was conducted with reference to the method described in "Standard methods for the examination of water and wastewater," 19th ed., American Public Health Association (APHA), New York, USA, (1995).

COMPARATIVE EXAMPLE 1

Anaerobic fermentative hydrogen production efficiency of conventional continuous stirred tank reactors I. Preparation of Seeding Culture Containing Biomasses:
   According to the heat pretreatment of seeding sludge in Item 3 under the preceding section B "General operating methods and equipment," the sewage sludge obtained from Li-ming municipal sewage treatment plant, Taichung City, was subjected to heat pretreatment at a temperature of 90° C. to 100° C. for approximately 30-60 minutes.
   Thereafter, the sewage sludge which was subjected to heat pretreatment was seeded into a continuous stirred tank reactor (CSTR) containing sucrose (at a concentration of 20 g COD/L, equivalent to 17.8 g/L) and nutrient salts, and was mixed therewith so as to form a mixture. Then, the mixture was acclimated at a temperature of 40° C. and at an agitation speed of 150 rpm for 8 to 24 hours, thereby forming a seeding culture containing biomasses.

II. Anaerobic Fermentative Hydrogen Producing Process:
   At an agitation speed of 150 rpm, sucrose (at a concentration of 20 g COD/L, equivalent to 17.8 g/L) was continuously fed into the continuous stirred tank reactor containing the aforesaid seeding culture (having biomasses formed therein), and anaerobic fermentative reactions were conducted in the continuous stirred tank reactor for 7 to 15 days at a hydraulic retention time of 12 hours (i.e., the organic loading rate was 1.67 g COD/L/h). Thereafter, the hydraulic retention time of the continuous stirred tank reactor was sequentially lowered to 8, 4, and 2 hours. Under a hydraulic retention time of 8 or 4 hours, the anaerobic fermentative reaction was allowed to proceed for 7 to 15 days. Under a hydraulic retention time of 2 hours, the anaerobic fermentative reaction was allowed to proceed for 2 to 3 days.

III. Results:

The gases and liquid effluents resulting from the anaerobic fermentative reactions were analyzed respectively according to the methods described in Item 4 (analysis of gas composition) and Item 5 (analysis of biomass concentration) under the preceding section B of "General operating methods and equipment." The data are expressed as mean±error (for different hydraulic retention times, the number of samples was about 3 to 8). The hydrogen production rate and the biomass concentration were plotted against the hydraulic retention time, and the results are shown in FIG. 1.

As shown in FIG. 1, when the hydraulic retention time of the continuous stirred tank reactor was reduced from 12 hours to 8 and 4 hours, the hydrogen production rate would increase with the reduction in hydraulic retention time, wherein when the hydraulic retention time was 4 hours (i.e., the organic loading rate was 5 g COD/L/h), the hydrogen production rate could reach 0.70 L/L/h. However, when the hydraulic retention time was reduced to 2 hours (i.e., the organic loading rate was 10 g COD/L/h), wash-out of the biomasses in the reactor would occur due to their ability to withstand the high dilution rate, which would lead to a reduction in the concentration of the hydrogen-producing anaerobic bacteria, thereby reducing the hydrogen production rate. The experimental results in FIG. 1 show that the conventional continuous stirred tank reactor is not suitable for operation under a low hydraulic retention time (i.e., a high organic loading rate).

EXAMPLE 1

Effect of Agitation Speed on Fermentative Hydrogen Production Process Using Continuous Stirred Tank Reactor This example investigates the effect of agitation speeds on the process of anaerobic fermentative hydrogen production with the use of a continuous stirred tank reactor.

I. Preparation of a Seeding Culture Containing Granular Biomasses:

The preparation of a seeding culture containing biomasses was made substantially in accordance with the operating procedures described in connection with the above comparative example 1. The difference resides in that the mixture was acclimated at an agitation speed of 30 rpm for approximately 8 to 24 hours so as to obtain a seeding culture containing granular biomasses.

II. Process of Anaerobic Fermentative Hydrogen Production:

At an agitation speed of 30 rpm, sucrose (at a concentration of 30 g COD/L, equivalent to 17.8 g/L) was continuously fed to the continuous stirred tank reactor containing the seeding culture (having the granular biomasses formed therein), and anaerobic fermentative reaction was allowed to proceed in the continuous stirred tank reactor at a hydraulic retention time of 8 hours (i.e., the organic loading rate was 2.5 g COD/L/h) for about 6 to 12 days. Thereafter, the agitation speed of the continuous stirred tank reactor was up-adjusted sequentially to 45 rpm and 90 rpm so that the anaerobic fermentative reaction was allowed to take place for 6 to 12 days under different agitation speeds.

The gas and the liquid effluents resulting from the anaerobic fermentative reactions were analyzed respectively according to the methods described in Item 4 (analysis of gas composition) and Item 5 (analysis of biomass concentration) under the preceding section B of "General operating methods and equipment." The data are expressed as mean±error (the number of samples was about 4 to 16 for different hydraulic retention times). The hydrogen production rate and the biomass concentration were plotted against the hydraulic retention time, and the results are shown in FIG. 2.

III. Results:

From the experimental results, it was found that when anaerobic fermentative reaction was conducted at an agitation speed of 30 rpm, the granular biomasses containing the hydrogen-producing anaerobic bacteria would increase with the progress of the reaction so that the concentration of the biomasses could reach 9.1 g VSS/L, and the hydrogen production rate could reach 0.58 L/L/h. In contrast, when the agitation speed of the continuous stirred tank reactor was increased to 45 rpm or even 90 rpm, both the concentration of the biomasses and the hydrogen production rate would drop with the increase in the agitation speed.

Figure 2:
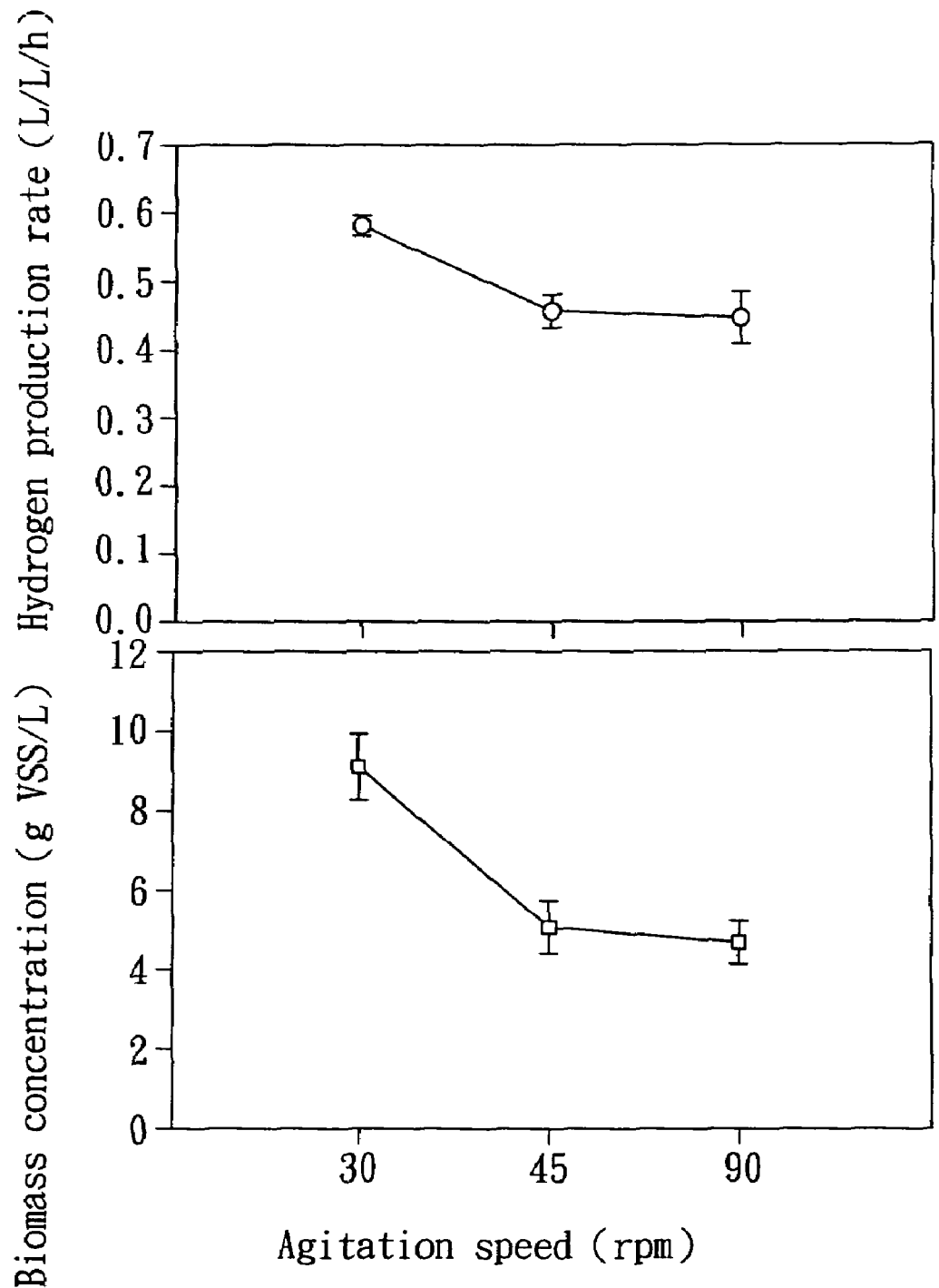
FIG. 2 shows the hydrogen production rates and the biomass concentrations (expressed in mean±standard error, number of samples being about 4 to 16) respectively detected when anaerobic fermentative reactions were carried out at a hydraulic retention time of 8 hours and at different agitation speeds, using sucrose (at a concentration of 20 g COD/L) as a substrate.

From the experimental results in FIG. 2, it is assumed that: when the continuous stirred tank reactor is operated at a relatively high agitation speed to carry out an anaerobic fermentative reaction, the granular biomasses will be affected and thus damaged by a high shear force, thereby reducing the hydrogen production rate. However, when the continuous stirred tank reactor is used to conduct an anaerobic fermentative reaction, a low agitation speed can assist in the formation of the granular biomasses and enhance the mixing effect of the reaction system, thereby enhancing the hydrogen production rate.

Therefore, in the following embodiments, the continuous stirred tank reactor was operated at a low agitation speed so as to further investigate the effect of the addition of a carrier on the anaerobic fermentative hydrogen production process.

EXAMPLE 2

The Effect of the Use of Glucose as a Substrate of Anaerobic Fermentative Reaction and the Use of Powdered Activated Carbon as a Carrier Upon the Anaerobic Fermentative Hydrogen Production Process This embodiment investigates the effect on the anaerobic fermentative hydrogen production process with the addition of a powdered activated carbon as a carrier for the hydrogen-producing anaerobic bacteria to adhere thereto and to proliferate thereon and under a low agitation speed and using glucose as the substrate of the anaerobic fermentative reaction.

I. Preparation of Seeding Culture Containing Granular Biomasses:

Sewage sludge obtained from Li-ming Sewage Treatment Plant, Taichung City, was subjected to heat pretreatment at a temperature of 90 to 100° C. for 30 to 60 minutes according to Item 3 "Heat pretreatment of seeding sludge under the preceding section "B. General operating methods and equipment."

Subsequently, the heat pretreated sewage sludge was mixed with a suitable amount (approx. 1 g/L) of powdered activated carbon, and was seeded into a continuous stirred tank reactor containing glucose (at a concentration of 20 g COD/L, equivalent to 18.75 g/L) and nutrient salts to be mixed homogenously therewith so as to form a mixture. In addition, the heat pretreated sewage sludge not added with powdered activated carbon was used as a control. Then, the mixture was acclimated at a temperature of 40° C. and an agitation speed of 15 to 20 rpm for about 8 to 24 hours to allow the hydrogen-producing anaerobic bacteria present in the heat pretreated sewage sludge to adhere to the powdered activated carbon and to proliferate thereon, thereby resulting in a seeding culture containing granular biomasses.

II. Anaerobic Fermentative Hydrogen Production Process:

Glucose (concentration: 20 g COD/L) was continuously fed to a continuous stirred tank reactor containing the above seeding culture (having the granular biomasses formed therein) at an agitation speed of 15 to 20 rpm, and anaerobic fermentative reaction was allowed to take place in the continuous stirred tank reactor under the condition of a 4-hour hydraulic retention time (i.e., the organic loading rate is 5 g COD/L/h).

Figure 3:
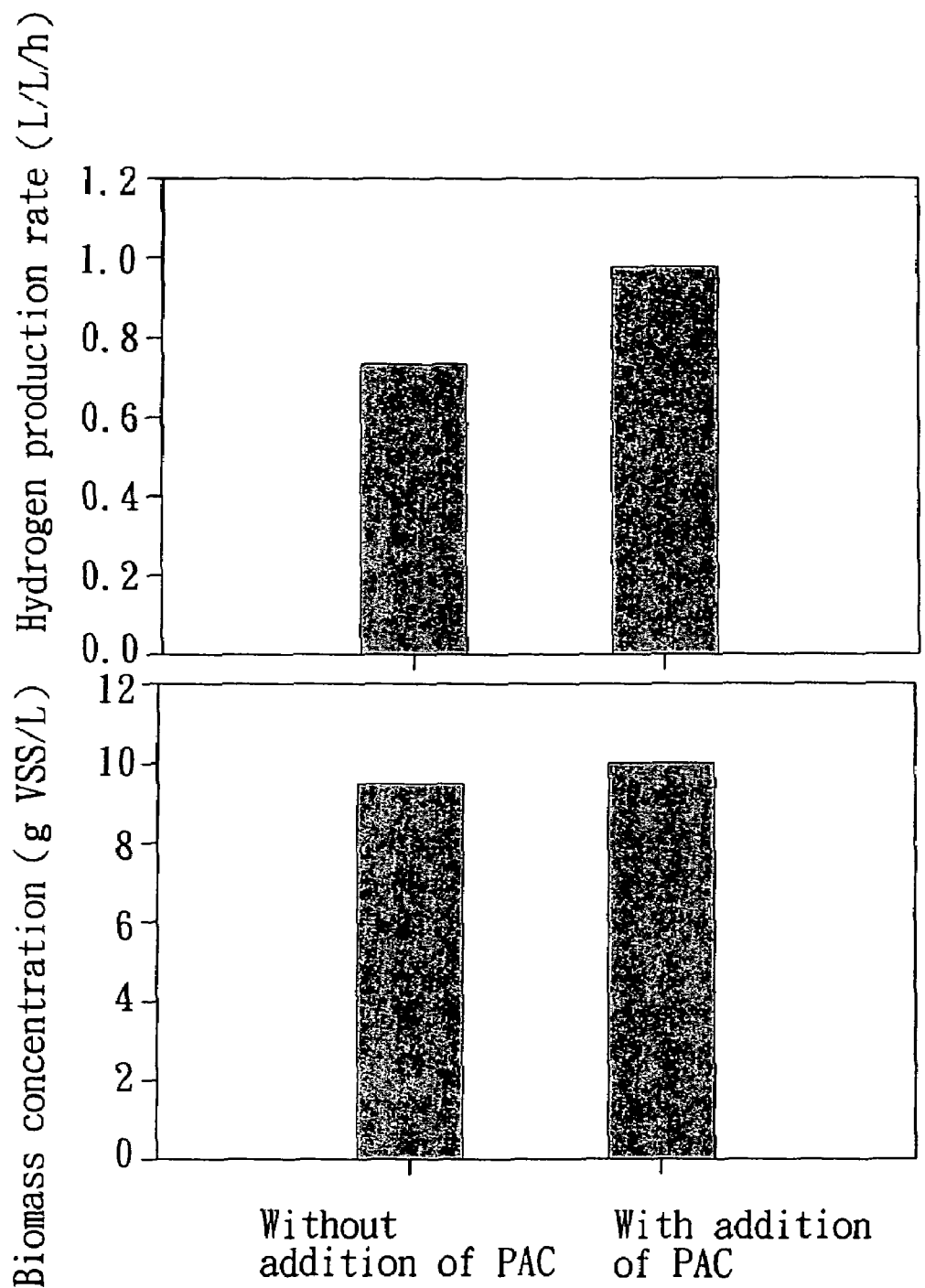
FIG. 3 shows the effect (expressed in mean values, number of samples being about 8 to 20) of addition of powdered activated carbon (PAC) on anaerobic fermentative hydrogen production when glucose (at a concentration of 20 g COD/L) was used as a substrate, the agitation speed was 15 to 20 rpm, and the hydraulic retention time was 4 hours.

When the operating system of the continuous stirred tank reactor reached a stable state, gas and liquid effluents produced by the anaerobic fermentative reaction were collected, and were analyzed according to the methods described in Item 4 "Analysis of gas composition" and Item 5 "Analysis of biomass concentration" under the preceding section "B. General operating methods and equipment." The data are expressed in means (the number of samples for each of the experimental group and the control group is 8 to 20). The hydrogen production rate and the biomass concentration were plotted against the addition of powdered activated carbon, and the results are shown in FIG. 3.

The hydrogen production efficiency of the anaerobic fermentative reaction system operated under a high organic loading rate and having powdered activated carbon added thereto and using glucose as a substrate is further investigated.

Figure 4:
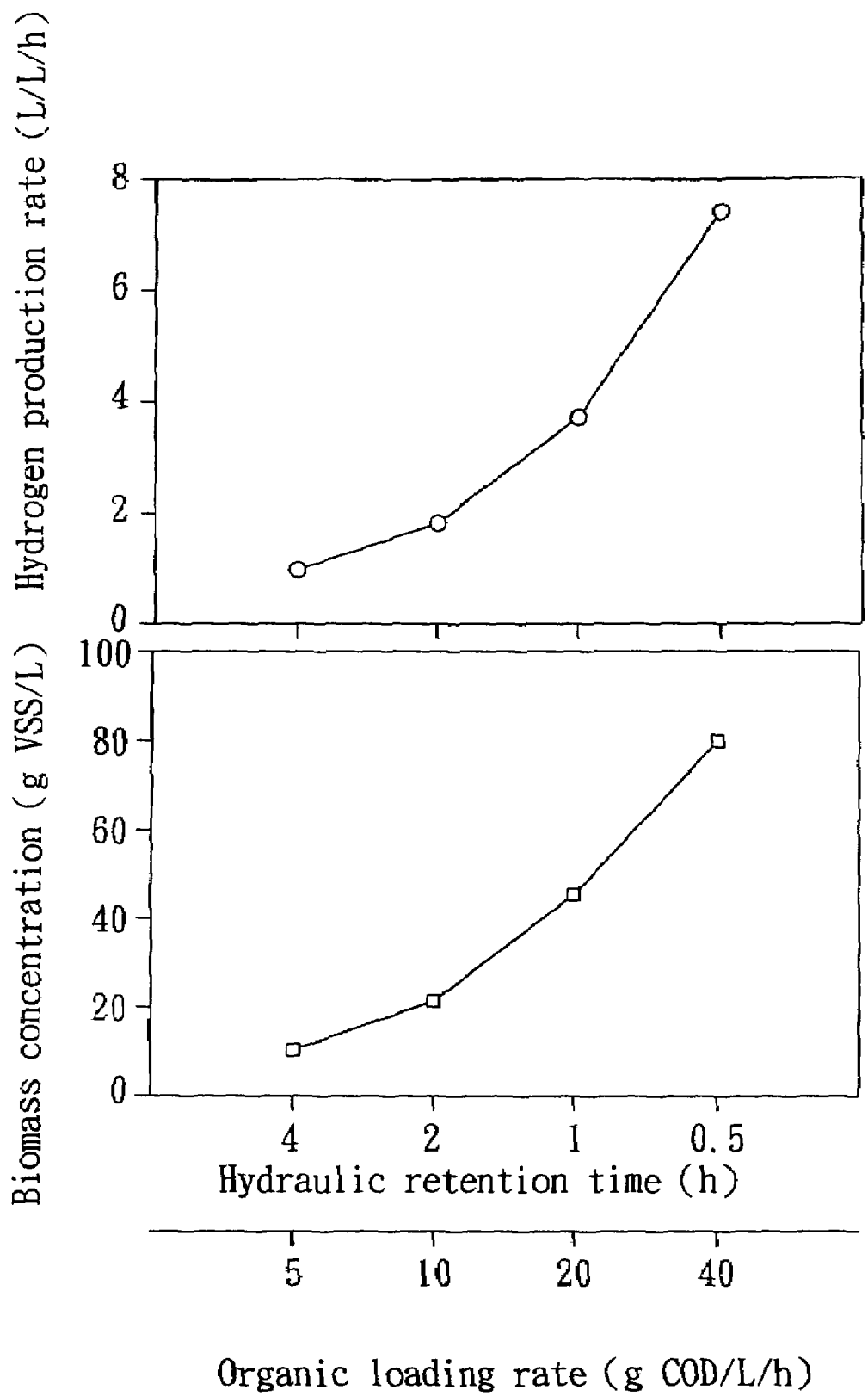
FIG. 4 shows the hydrogen production rates and the biomass concentrations (expressed in mean values, number of samples being about 8 to 25) detected when anaerobic fermentative reactions were carried out in an anaerobic fermentative reaction system added with powdered activated carbon (PAC) and using glucose as a substrate at an agitation speed of 15 to 20 rpm and at different hydraulic retention times.

The hydraulic retention times of the anaerobic fermentative reaction system added with powdered activated carbon (PAC) were down-adjusted sequentially to 2, 1 and 0.5 hour (i.e., the organic loading rates were increased sequentially to 10, 20 and 40 g COD/L/h), and anaerobic fermentative reaction was conducted under each of the set hydraulic retention times for 15 to 30 days. The gas and liquid effluents resulting from the anaerobic fermentative reaction were collected, and were analyzed respectively according to the methods described in Item 4 (analysis of gas composition) and Item 5 (analysis of biomass concentration) under the preceding section B of "General operating methods and equipment." The data are expressed as mean±error (the number of samples was about 8 to 25 for different hydraulic retention times). The hydrogen production rate and the biomass concentration were plotted against the hydraulic retention time/organic loading rate, and the results are shown in FIG. 4.

III. Results:

It can be seen from FIG. 3 that the detected biomass concentration and the hydrogen production rate of the anaerobic fermentative hydrogen production system without addition of powdered activated carbon are 9.5 g VSS/L and 0.73 L/L/h, respectively. It is assumed that the operating strategy of a low agitation speed contributed to the formation of the granular biomasses, which was conducive to the smooth operation of the anaerobic fermentative hydrogen production system operated at a low hydraulic retention time.

In addition, the detected biomass concentration and the hydrogen production rate of the anaerobic fermentative hydrogen production system with addition of powdered activated carbon are 10.0 g VSS/L and 0.97 L/L/h, respectively. It is hence apparent that the operating strategy of a low agitation speed combined with the addition of a carrier can increase the concentration of granular biomasses containing hydrogen-producing anaerobic bacteria, thereby further enhancing the hydrogen production rate.

It is evident from FIG. 4 that the hydrogen production rate and the biomass concentration would be increased with the down-adjustment of the hydraulic retention time, wherein when hydraulic retention time was 0.5 hour (i.e., the organic loading rate is 40 g COD/L/h), the detected biomass concentration was as high as 80 g VSS/L, and the hydrogen production rate could reach 7.33 L/L/h. These results show that the operating strategy of adding powdered activated carbon in combination with a low agitation speed enables the anaerobic fermentation system to conduct anaerobic fermentative reaction with stability under a low hydraulic retention time (i.e., a high organic loading rate), and increases the hydrogen production rate.

EXAMPLE 3

Effect of the Combination of a Low Agitation Speed and Addition of Powdered Activated Carbon on Anaerobic Fermentation Process Using Sucrose as a Substrate This example investigates the effect of the addition of powdered activated carbon as a carrier for the hydrogen-producing anaerobic bacteria to adhere thereto and to proliferate thereon and a low agitation speed on the anaerobic fermentative hydrogen production process using sucrose as a substrate for the anaerobic fermentative reaction.

I. Preparation of a Seeding Culture Containing Granular Biomasses:

The preparation of a seeding culture containing granular biomasses was essentially made with reference to the operating procedures described in the above Example 2. The difference resides in that an upflow anaerobic sludge blanket (UASB) having a working volume of 1.25 L and fitted with a stirrer was used, and sucrose (at a concentration of 20 g COD/L, equivalent to 17.8 g/L) was used to acclimate the mixture for 8 to 24 hours to result in a seeding culture containing granular biomasses.

II. Anaerobic Fermentative Hydrogen Production Process:

Sucrose (at a concentration of 20 g COD/L, equivalent to 17.8 g/L) was continuously fed to the upflow anaerobic sludge blanket containing the above seeding culture (having granular biomasses formed therein) at an agitation speed of 15 to 20 rpm, and anaerobic fermentative reaction was carried out in the upflow anaerobic sludge blanket operated at a hydraulic retention time (i.e., the organic loading rate is 5 g COD/L/h) of 4 hours for 7 to 20 days.

Thereafter, the hydraulic retention times of the upflow anaerobic sludge blanket were down-adjusted sequentially to 2, 1 and 0.5 hr. (i.e., the organic loading rates were increased sequentially to 10, 20 and 40 g COD/L/h), and anaerobic fermentative reactions were respectively carried out at different hydraulic retention times for 7 to 20 days.

In addition, to investigate the effect of increasing the biomass concentration so as to increase the organic loading rate on hydrogen production efficiency, sucrose concentration was up-adjusted sequentially to 30 and 40 g COD/L (i.e., the organic loading rate was increased sequentially to 60 and 80 g COD/L/h) at a hydraulic retention time of 0.5 hr., and anaerobic fermentative reactions were each carried out for 15 to 30 days.

The gases and liquid effluents resulting from the anaerobic fermentative reaction were collected, and were analyzed respectively according to the method described in Item 4 (analysis of gas composition) and Item 5 (analysis of biomass concentration) under the preceding section B of "General Operating methods and equipment." The data are represented as mean±error (for different hydraulic retention times, the number of samples was about 3 to 25). The hydrogen production rate (HPR) and the biomass concentration were plotted against hydraulic retention time/organic loading rate, and the results are shown in FIG. 5.

Figure 5:
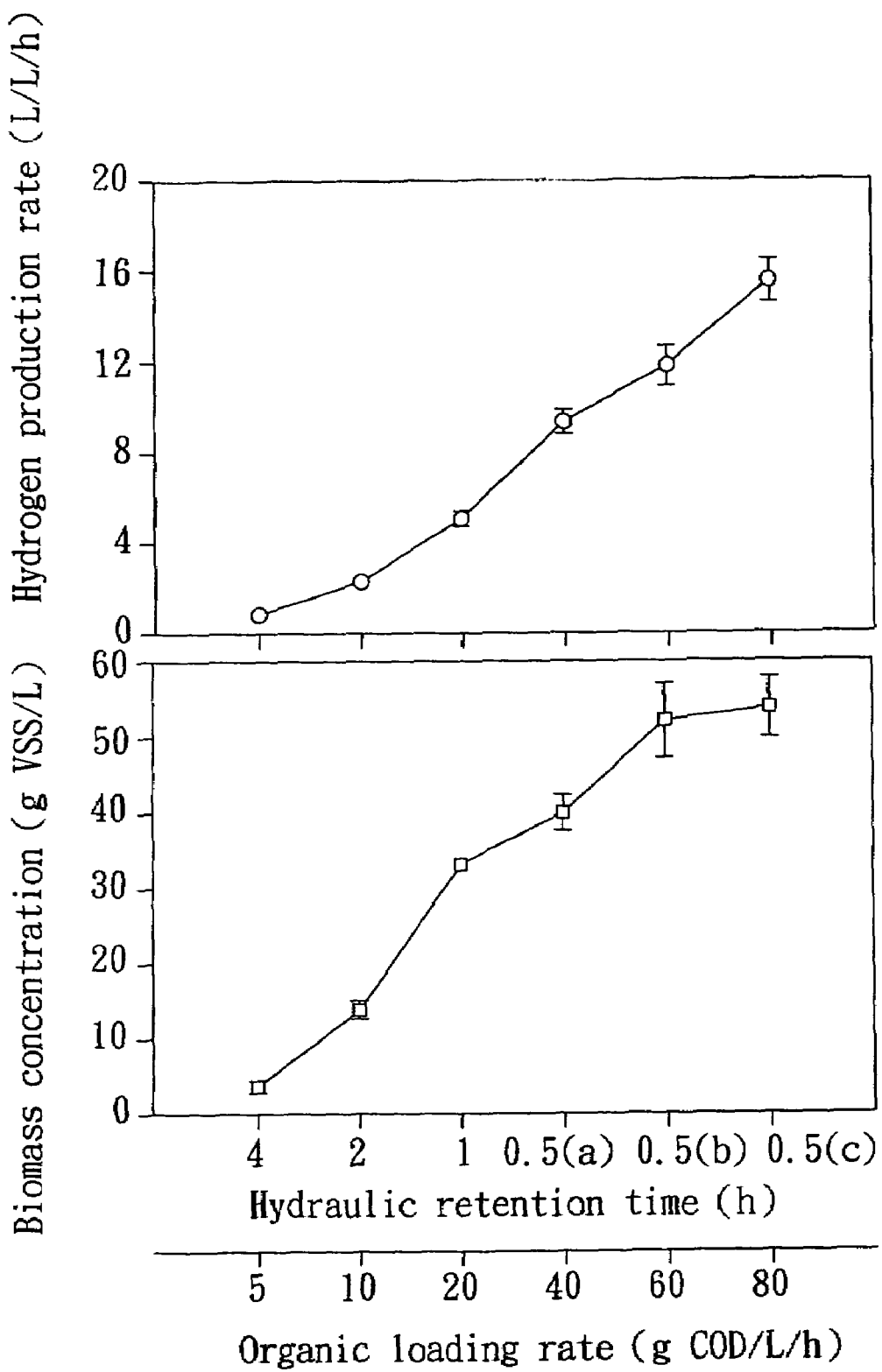
FIG. 5 shows the hydrogen production rates and biomass concentrations (expressed in mean±standard error, the number of samples being about 3 to 25) detected when anaerobic fermentative reactions were carried out at an agitation speed of 15 to 20 rpm and at different organic loading rates in an anaerobic fermentative reaction system added with powdered activated carbon and using glucose as a substrate, wherein 0.5 (a) represents: HRT=0.5 hr., and sucrose concentration=20 g COD/L; 0.5(b) represents: HRT=0.5 hr., and sucrose concentration=30 g COD/L; and 0.5(c) represents: HRT=0.5 hr., and sucrose concentration=40 g COD/L.

III. Results:

From FIG. 5, it can be seen that the hydrogen production rate and the biomass concentration will be increased with a reduction in the hydraulic retention time (i.e., an increase in the organic loading rate), wherein when the hydraulic retention time was 0.5 hour (the organic loading rate was 40 g COD/L/h), the detected biomass concentration was about 40 g VSS/L, whereas the hydrogen production rate could reach 9.31 L/L/h.

In addition, when the sucrose concentration was increased sequentially to 30 and 40 g COD/L (i.e., the organic loading rate was increased sequentially to 60 and 80 g COD/L/h), the detected biomass concentrations were about 52 and 54 g VSS/L, respectively, and the hydrogen production rates were 11.7 and 15.3 L/L/h, respectively.

The above results show that the anaerobic fermentative reaction system according to the present invention can achieve a high hydrogen production efficiency and stable hydrogen production by increasing the organic loading rate of the reaction system whether through reducing the hydraulic retention time or increasing the biomass concentration.

All patents and literature references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:

1. A process for enhancing anaerobic biohydrogen production, comprising:
    adding into a reactor an organic waste containing hydrogen-producing anaerobic bacteria, a first substrate, and a carrier that permits the hydrogen-producing anaerobic bacteria to adhere and grow thereon, so as to form a mixture;
    acclimating the mixture at a first agitation speed ranging from 5 to 60 rpm, so that the hydrogen-producing anaerobic bacteria adhere to and proliferate on the carrier, followed by the formation of granular biomasses constituted of the hydrogen-producing anaerobic bacteria within the acclimated mixture; and
    feeding a second substrate into the reactor at a second agitation speed ranging from 5 to 60 rpm, so that the content of the granular biomasses is increased while the second substrate is anaerobically fermented by the hydrogen-producing anaerobic bacteria in the granular biomasses to result in the production of hydrogen.

2. The process according to claim 1, wherein the organic waste is selected from the group consisting of sewage sludge from household sewage treatment plants, sewage sludge from fermentation-related industries, sewage sludge from paper manufacturing industries, sewage sludge from sugar manufacturing industries, sewage sludge from food factories, and combinations thereof.

3. The process according to claim 1, wherein the organic waste undergoes a pretreatment selected from the group consisting of heating, acclimation, treatment with a pH adjusting agent, and combinations thereof, so that the hydrogen-producing anaerobic bacteria present in the organic waste are dominant.

4. The process according to claim 3, wherein the organic waste is subjected to a heat pretreatment.

5. The process according to claim 4, wherein the organic waste is subjected to heat pretreatment at a temperature ranging from 90 to 100° C. for 30 to 60 minutes.

6. The process according to claim 3, wherein the organic waste is subjected to a pretreatment using an acidic pH adjusting agent so as to have a pH value ranging from 3 to 5.

7. The process according to claim 6, wherein the acidic pH adjusting agent is selected from the group consisting of hydrochloric acid, sulfuric acid, nitric acid, and combinations thereof.

8. The process according to claim 3, wherein the organic waste is subjected to a pretreatment using a basic pH adjusting agent so as to have a pH value ranging from 10 to 12.

9. The process according to claim 8, wherein the basic pH adjusting agent is selected from the group consisting of NaOH, KOH, LiOH, Ca(OH)$_2$, Mg(OH)$_2$, and combinations thereof.

10. The process according to claim 1, wherein the first substrate and the second substrate are independently selected from the group consisting of an artificial substrate and an organic waste.

11. The process according to claim 10, wherein the artificial substrate includes a saccharide selected from the group consisting of glucose, fructose, xylose, sucrose, maltose, starch, and combinations thereof.

12. The process according to claim 11, wherein the artificial substrate includes one of glucose and sucrose.

13. The process according to claim 10, wherein the organic waste suitable for the front and second substrates is selected from the group consisting of sewage sludge from household sewage treatment plants, sewage sludge from fermentation-related industries, sewage sludge from sugar manufacturing industries, sewage sludge from food factories, and combinations thereof.

14. The process according to claim 1, wherein the carrier is a microporous adsorbent.

15. The process according to claim 14, wherein the microporous adsorbent has a particle size less than 44 microns.

16. The process according to claim 15, wherein the microporous adsorbent is selected from the group consisting of powdered activated carbon, powdered diatomaceous earth, zeolite, and combinations thereof.

17. The process according to claim 1, wherein the reactor is selected from the group consisting of a continuous stirred tank reactor, an anaerobic sequencing batch reactor, an anaerobic baffled bioreactor, a carrier-induced granular sludge bed, an upflow anaerobic sludge blanket, an expanded granular sludge bed, and combinations thereof.

18. The process according to claim 1, wherein the reactor is placed in an anaerobic state by evacuation.

19. The process according to claim 1, wherein the reactor is placed in an anaerobic state by filling the reactor with an inert gas.

20. The process according to claim 19, wherein the inert gas is selected from the group consisting of helium, argon, neon, krypton, xenon, and combinations thereof.

21. The process according to claim 1, wherein the first agitation speed and the second agitation speed are independently set to fall within a range from 15 to 20 rpm.

22. The process according to claim 1, wherein the second substrate is fed into the reactor at a hydraulic retention time ranging from 0.5 to 8 hours.

23. The process according to claim 1, wherein the second substrate is fed into the reactor at an organic loading rate ranging from 5 to 80 g COD/L/h.

* * * * *